US011697893B2

(12) United States Patent
Rothenburger-Glaubitt et al.

(10) Patent No.: US 11,697,893 B2
(45) Date of Patent: Jul. 11, 2023

(54) HIGHLY FLEXIBLE DEGRADABLE FIBERS

(71) Applicant: FRAUNHOFER-GESELLSCHAFT ZUR FÖRDERUNG DER ANGEWANDTEN FORSCHUNG E. V., Munich (DE)

(72) Inventors: Miranda Rothenburger-Glaubitt, Margetshöchheim (DE); Bastian Christ, Würzburg (DE); Walther Glaubitt, Margetshöchheim (DE); Jörn Probst, Kürnach (DE)

(73) Assignee: Fraunhofer-Gesellschaft zur förderung der angewandten Forschung e.V., Munich (DE)

( * ) Notice: Subject to any disclaimer, the term of this patent is extended or adjusted under 35 U.S.C. 154(b) by 42 days.

(21) Appl. No.: 16/652,099

(22) PCT Filed: Sep. 26, 2018

(86) PCT No.: PCT/EP2018/076106
§ 371 (c)(1),
(2) Date: Mar. 30, 2020

(87) PCT Pub. No.: WO2019/068533
PCT Pub. Date: Apr. 11, 2019

(65) Prior Publication Data
US 2020/0308729 A1    Oct. 1, 2020

(30) Foreign Application Priority Data

Oct. 2, 2017   (DE) ................. 10 2017 217 539.9

(51) Int. Cl.
*D01F 6/76*     (2006.01)
*C12N 5/00*    (2006.01)
*C12N 5/077*   (2010.01)

(52) U.S. Cl.
CPC ............ *D01F 6/76* (2013.01); *C12N 5/0068* (2013.01); *C12N 5/0656* (2013.01); *C12N 2533/20* (2013.01); *C12N 2537/10* (2013.01); *C12N 2539/00* (2013.01); *D10B 2401/12* (2013.01)

(58) Field of Classification Search
None
See application file for complete search history.

(56) References Cited

U.S. PATENT DOCUMENTS

| | | |
|---|---|---|
| 8,206,675 B2 | 6/2012 | Thierauf |
| 8,956,987 B2 | 2/2015 | Durschang et al. |
| 9,125,812 B2 | 9/2015 | Durschang et al. |
| 9,206,077 B2 | 12/2015 | Durschang et al. |
| 9,604,873 B2 | 3/2017 | Durschang et al. |
| 9,730,863 B2 | 8/2017 | Durschang et al. |
| 9,862,940 B2 | 1/2018 | Glaubitt |
| 10,064,974 B2 | 9/2018 | Gerber |
| 10,357,343 B2 | 7/2019 | Durschang et al. |
| 10,442,725 B2 | 10/2019 | Durschang et al. |
| 2010/0174045 A1 | 7/2010 | Thierauf |
| 2010/0193304 A1 | 8/2010 | Bose et al. |
| 2011/0183419 A1 | 7/2011 | Glaubitt |
| 2012/0309607 A1 | 12/2012 | Durschang et al. |
| 2013/0145964 A1* | 6/2013 | Barth ............. C01B 33/148 106/287.34 |
| 2013/0295523 A1 | 11/2013 | Durschang et al. |
| 2014/0031452 A1 | 1/2014 | Gerber |
| 2014/0037958 A1 | 2/2014 | Gerber |
| 2014/0200129 A1 | 7/2014 | Durschang et al. |
| 2014/0252272 A1 | 9/2014 | Durschang et al. |
| 2015/0246843 A1 | 9/2015 | Durschang et al. |
| 2015/0376053 A1 | 12/2015 | Durschang et al. |
| 2018/0155234 A1 | 6/2018 | Durschang et al. |
| 2018/0344895 A1 | 12/2018 | Gerber |

FOREIGN PATENT DOCUMENTS

| | | |
|---|---|---|
| DE | 196 09 551 C1 | 7/1997 |
| DE | 102007061873 A1 | 7/2008 |
| DE | 102014224654 A1 | 6/2016 |
| EP | 2 152 785 A1 | 2/2010 |
| WO | WO 2008/148384 A1 | 12/2008 |
| WO | WO 2012/104320 A1 | 8/2012 |

OTHER PUBLICATIONS

Appendix 5 Chem 1A, B, C, Lab Manual and Zumdahl 6th Ed., Table of Acids with Ka and pKa Values, 2 pages, retreived from the internet (Oct. 8, 2021): http://clas.sa.ucsb.edu/staff/Resource%20folder/Chem109ABC/Acid,%20Base%20Strength/Table%20of%20Acids%20w%20Kas%20and%20pKas.pdf (Year: 2021).*
Hromadko et al., ACS Omega 2017, 2, 8, 5052-5059 (Year: 2017).*
Yao et al., Composites: Part B 69 (2015) 478-483 (Year: 2015).*
Tran et al., Advances in Natural Sciences: Nanoscience and Nanotechnology 4 (2013) 045007 (6 pages) (Year: 2013).*
Emmert et al., "Nanostructured surfaces of biodegradable silica fibers enhance directed amoeboid cell migration in a microtubule-dependent process," *RSC Adv* 7: 5708-5714 (2017).
German Patent Office, Office Action in German Patent Application No. 10 2017 217 539.7 (dated Mar. 26, 2018).
European Patent Office, International Search Report in International Application No. PCT/EP2018/076106 (dated Dec. 10, 2018).
European Patent Office, Written Opinion in International Application No. PCT/EP2018/076106 (dated Dec. 10, 2018).
International Bureau of WPIO, International Preliminary Report in International Application No. PCT/EP2018/076106 (dated Apr. 8, 2020).

(Continued)

*Primary Examiner* — Evelyn Y Pyla
(74) *Attorney, Agent, or Firm* — Leydig, Voit & Mayer, Ltd.

(57) ABSTRACT

The present invention relates to a method for producing biodegradable fibers on the basis of a silane compound, said silane compound being crosslinked during production and, at least to some extent, an organic acid being incorporated into the forming crosslinked structure via covalent bonds and/or contributing to the crosslinking. The present invention also relates to the fibers that can be produced by the method according to the invention and to the use thereof.

14 Claims, 4 Drawing Sheets

(56) References Cited

OTHER PUBLICATIONS

U.S. Appl. No. 12/595,655, filed Oct. 13, 2009.
U.S. Appl. No. 13/518,765, filed Jun. 22, 2012.
U.S. Appl. No. 13/880,894, filed Apr. 22, 2013.
U.S. Appl. No. 14/127,040, filed Dec. 17, 2013.
U.S. Appl. No. 14/127,048, filed Dec. 17, 2013.
U.S. Appl. No. 14/586,229, filed Dec. 30, 2014.
U.S. Appl. No. 14/846,286, filed Sep. 4, 2015.
U.S. Appl. No. 15/401,380, filed Jan. 9, 2017.

* cited by examiner

HIGHLY FLEXIBLE DEGRADABLE FIBERS

CROSS-REFERENCE TO RELATED APPLICATIONS

This patent application is the U.S. national phase of International Application No. PCT/EP2018/076106, filed on Sep. 26, 2018, which claims the benefit of German Patent Application No. 10 2017 217 539.7, filed Oct. 2, 2017, the disclosures of which are incorporated herein by reference in their entireties for all purposes.

The present invention relates to processes for producing highly flexible biodegradable fibres and to the fibres and fibre meshes produced therefrom by the process of the invention. In addition, the present invention relates to the use of biodegradable fibres or fibre meshes in the fields of regenerative therapies, microbiology, pharmaceutical uses, cosmetics industry, diagnostics, food industry, filters, fibre reinforcement of materials and optics.

BACKGROUND OF THE INVENTION

Microfibres and nanofibres are used in many fields of healthcare such as regenerative medicine, treatment, diagnostics, in the pharmaceutical industry and in the food industry.

A biodegradable fibre, the degradation products of which are non-toxic under physiological conditions, is suitable, for example, for use as a cell-support material in vitro or in vivo in regenerative medicine, treatment and diagnostics.

The biocompatibility of silicon dioxide makes $SiO_x$-based fibre materials of great interest here. Many of these materials are used in biology, medicine and in the food and pharmaceutical industries, but are mostly not biodegradable. The few known biodegradable $SiO_x$ fibre systems have low flexibility and a high tendency to become brittle.

An example of the in-vivo use of fibre meshes is as a cell-support structure in a tissue defect. However, once applied to the tissue defect, the fibres very readily become brittle, which compromises the ability of the fibre structure to provide the necessary support for the development of new tissue.

The brittleness of such fibres is also beset by practical problems when used in vitro. For example, the non-destructive removal of such fibres from a multiwell plate is possible only with great difficulty.

There is particular interest in finding biodegradable materials that degrade in a period of >6 months for uses in regenerative medicine. The period over which the degradation of the fibres takes place is strongly dependent on how much fibre is applied and on the volume of body fluids present at the application site. It is accordingly also possible to consider very long degradation periods of more than 3 years, for example. However, it is preferable that the fibre degrades in a period of from 6 to 18 months, more preferably of from 10 to 12 months. Most fibre materials developed thus far are broken down within a few days or weeks or are stable in the long term (several years).

EP 2 152 785 A1 relates to a polyethoxysiloxane (PES) material that can be obtained by (a) carrying out an initial hydrolysis-condensation reaction (HCR) of at most one radical X of one or more different Si compounds of the formula I SiX4 (I), in which the radicals X are identical or different and represent hydroxy, hydrogen or ethoxy (EtO), under acid catalysis at an initial pH from 0 to 7, in the presence of ethanol (EtOH) or an ethanol-water mixture as solvent, over a period of 1 to 24 h at a temperature of 0° C. to 78° C., (b) carrying out a second HCR on the material obtained in step (a), with simultaneous removal of the solvent by successive evaporation in a container impermeable to gaseous diffusion at a pressure of 100 to 1013 mbar; preferably at a slight underpressure of 300 mbar to 800 mbar and at a temperature of 50 to 78° C. until a sharp increase in viscosity (at a shear rate of $10\ s^{-1}$ at 4° C.) to 0.5 to 2 Pa·s, until constant weight and until the formation of a cyclotetrasiloxane of the general formula $((Si)(OH)_{0.75}(OEt)_{1.25} \cdot 1/64 H_2O)_4$ and having a molar mass of 4*approx. 114 g=approx. 456 g, (c) cooling this PES material in a closed container over a period of a few minutes to a few seconds and (d) converting the PES material obtained from (c) into an rPES material by means of a third HCR.

DE 10 2014 224 654 A1 describes a biodegradable silicate hybrid material comprising silsesquioxanes and an organic multi-arm linker, with the organic multi-arm linker including at least one of the compounds I and being covalently attached to the silsesquioxanes.

The known biodegradable fibres of the prior art degrade within a few days or are stable in the long term (>3 years). In addition, these fibres do not have the required mechanical properties and in particular do not have sufficiently high mechanical flexibility. Improvements in the biocompatibility of the fibres and in the proliferation of human fibroblasts on these fibres are also needed.

BRIEF SUMMARY OF THE INVENTION

On this basis, the object of the present invention was to provide a process with which it is possible to produce fibres that degrade in a period of 6 to 18 months and that additionally have very good textile mechanical properties, high mechanical flexibility in particular. A further object was to provide fibres having improved biocompatibility, especially as determined in accordance with DIN ISO 10993-5, and increased proliferation of human fibroblasts on the fibres.

This object is achieved by the process for producing biodegradable fibres described herein, which comprises the following steps:

a) providing at least one alcoholic solution of at least one silane compound selected from the group consisting of tetraalkoxysilanes, trialkoxysilanes, halosilanes and mixtures thereof;

b) providing an aqueous solution of at least one organic acid having a pKa of <2.0;

c) combining the solutions provided in steps a) and b) and mixing for 4 hours to 1 week at a temperature of 20 to 70° C.;

d) removing at least part of the alcohol from the mixture from step c) and then cooling the concentrated mixture to a temperature of 20 to −25° C.;

e) storing the cooled mixture from step d) until a viscosity of 10 to 75 Pa·s is reached;

f) spinning the mixture from step e) into continuous fibres; wherein during steps c) to e), the silane compound undergoes cross-linking and at least part of the organic acid is incorporated into the resulting network via covalent bonds and/or contributes to the crosslinking.

Preferred embodiments of the biodegradable fibres of the invention are also described herein.

The invention relates to a fibre produced by the process of the invention. Preferred embodiments of the biodegradable fibres of the invention are also described herein.

The invention also relates to fibre meshes and filters made from the fibres of the invention and further relates to uses of the biodegradable fibres and of the fibre meshes.

DETAILED DESCRIPTION OF EMBODIMENTS OF THE INVENTION

Definitions of Terms

A "biodegradable" fibre in the context of the present invention means a fibre that is biocompatible and that is broken down under physiological conditions.

In the context of the present invention, the term "viscosity" means the dynamic viscosity, which is preferably determined using a Physica MCR301 rheometer from Anton Paar equipped with a CC17/T200/S coaxial cylinder measuring attachment at a shear rate of 10 s$^{-1}$.

The "crosslinking of the silane compound" and the covalent incorporation of the organic acid into the network is illustrated in the following diagram taking the incorporation of methanesulfonic acid as an example.

The term "coilable fibre" is understood as meaning a fibre that can be coiled onto a reel without the fibre being destroyed in the process.

Process

In a preferred embodiment of the present invention, the silane compound selected in step a) is a mixed or unmixed tetraalkoxysilane corresponding to the general formula $Si(OC_xH_{2x+1})_4$ where x=1-12, which is preferably selected from the group consisting of tetraethoxysilane, tetrapropoxysilane, tetrabutoxysilane and mixtures thereof, wherein particular preference is given to tetraethoxysilane.

Another preferred embodiment of the present invention envisages that the alcohol from step a) is a monohydric, dihydric or trihydric, branched or unbranched alcohol that may be aliphatic or aromatic and is preferably selected from the group consisting of ethanol, propanol, butanol, ethylene glycol, phenol and mixtures thereof, wherein preference is given to ethanol.

According to another preferred embodiment of the present invention, the silane compound selected in step a) is a mixed or unmixed tetraalkoxysilane corresponding to the general formula $Si(OC_xH_{2x+1})_4$ where x=1-12, which is preferably selected from the group consisting of tetraethoxysilane, tetrapropoxysilane, tetrabutoxysilane and mixtures thereof, wherein particular preference is given to tetraethoxysilane and the alcohol from step a) is a monohydric, dihydric or trihydric, branched or unbranched alcohol that may be aliphatic or aromatic and is preferably selected from the group consisting of ethanol, propanol, butanol, ethylene glycol, phenol and mixtures thereof, wherein preference is given to ethanol.

Another preferred embodiment of the present invention envisages that the organic acid in step b) is selected from the group consisting of sulfonic acids, in particular methanesulfonic acid, carboxylic acids, carboxylic esters, sulfuric esters, amino acids, phosphonic acids, phosphoric esters and mixtures thereof, wherein particular preference is given to methanesulfonic acid.

According to another preferred embodiment of the present invention, the organic acid in step b) is 0.01 to 1 N and more preferably 0.1 N.

Another preferred embodiment envisages that the content of organic acid in the aqueous solution from step b) is in the range from 0.01 to 2% by weight, preferably 0.05 to 1% by weight and more preferably 0.1 to 0.5% by weight, based on the total weight of the solution.

In another preferred embodiment of the present invention, the organic acid in step b) is selected from the group consisting of sulfonic acids, in particular methanesulfonic acid, carboxylic acids, carboxylic esters, sulfuric esters, amino acids, phosphonic acids, phosphoric esters and mixtures thereof, wherein particular preference is given to methanesulfonic acid, and the organic acid in step b) is 0.01 to 1 N, more preferably 0.1 N.

According to another preferred embodiment of the present invention, the organic acid in step b) is selected from the group consisting of sulfonic acids, in particular methanesulfonic acid, carboxylic acids, carboxylic esters, sulfuric esters, amino acids, phosphonic acids, phosphoric esters and mixtures thereof, wherein particular preference is given to methanesulfonic acid, and the organic acid in step b) is 0.01 to 1 N, more preferably 0.1 N, and the content of organic acid in the aqueous solution from step b) is in the range from 0.01 to 2% by weight, preferably 0.05 to 1% by weight and more preferably 0.1 to 0.5% by weight, based on the total weight of the solution.

Another preferred embodiment of the present invention envisages that the mixing in step c) is carried out by adding the aqueous solution of the organic acid dropwise to the alcoholic silane solution or the mixing in step c) is carried out by adding the alcoholic silane solution dropwise to the aqueous solution of the organic acid or the mixing in step c) is carried out by simultaneous combination of the alcoholic silane solution and the aqueous solution of the organic acid.

In another preferred embodiment of the present invention, the mixing in step c) is carried out by stirring or shaking.

According to another preferred embodiment of the present invention, the mixture from step c) is stirred for 5 hours to 144 hours, preferably 10 to 24 hours and more preferably for 16 to 18 hours.

Another preferred embodiment of the present invention envisages that the temperature in step c) is 20 to 60° C., preferably 20 to 50° C. and more preferably 25 to 40° C.

In another preferred embodiment of the present invention, the pH of the mixture in step c) is <5, preferably 1 to 4.9 and more preferably 4 to 4.9.

Another preferred embodiment of the present invention envisages that the mixing in step c) is carried out by adding the aqueous solution of the organic acid dropwise to the alcoholic silane solution or the mixing in step c) is carried out by adding the alcoholic silane solution dropwise to the aqueous solution of the organic acid or the mixing in step c) is carried out by simultaneous combination of the alcoholic silane solution and the aqueous solution of the organic acid and the mixing in step c) is carried out by stirring and the mixture from step c) is stirred for 5 hours to 144 hours, preferably 10 to 24 hours and more preferably for 16 to 18 hours and the temperature in step c) is 20 to 60° C., preferably 20 to 50° C. and more preferably 25 to 40° C. and the pH of the mixture in step c) is <5, preferably 1 to 4.9 and more preferably 4 to 4.9.

In another preferred embodiment of the present invention, during step d) 40 to 80% by weight, preferably 45 to 75% by weight and more preferably 50 to 65% by weight, of the solvent mixture, based on the total mass of mixture provided in step b), is removed.

According to another preferred embodiment of the present invention, the concentrated mixture from step d) is cooled to a temperature of 20 to −25° C., preferably 10 to −25° C. and more preferably 4 to −20° C.

Another preferred embodiment envisages that at least part of the water from step b) is also removed during step d).

In another preferred embodiment of the present invention, during step d) 40 to 80% by weight, preferably 45 to 75% by weight and more preferably 50 to 65% by weight, of the solvent mixture, based on the total mass of mixture provided in step b), is removed and the concentrated mixture from step d) is cooled to a temperature of 20 to −25° C., preferably 10 to −25° C. and more preferably 4 to −20° C. and at least part of the water from step b) is removed.

In another preferred embodiment of the present invention, step e) is carried out until a viscosity of 10 to 70 Pa·s, preferably 10 to 40 Pa·s and more preferably 20 to 25 Pa·s is reached.

Another preferred embodiment of the present invention envisages that spinning is carried out with the application of pressure in the range from 10 to 60 bar, preferably 10 to 40 bar and more preferably 20 to 40 bar.

Another preferred embodiment of the present invention envisages that the process comprises the following further process steps, which take place after step f):

g) cutting or stamping the continuous fibres obtained after spinning in step f), and/or h) sterilizing the fibres from step f) or g), preferably by γ-radiation or by treatment with ethylene oxide, 70% ethanol solution or chloroform.

According to another preferred embodiment of the present invention, exactly one alcohol is used as the solvent in step a).

Another preferred embodiment of the present invention envisages that exactly one silane compound is dissolved in the solution according to step a).

In another preferred embodiment of the present invention, an aqueous solution of exactly one organic acid is provided in step b).

Another preferred embodiment of the present invention envisages that exactly one alcohol is used as solvent in step a) and exactly one silane compound is dissolved in the solution according to step a) and an aqueous solution of exactly one organic acid is provided in step b).

In another preferred embodiment of the present invention, the process is carried out as a continuous or batchwise operation.

According to another preferred embodiment of the present invention, the process comprises no process steps other than steps a) to h) mentioned above.

Biodegradable Fibres

The present invention further relates to a fibre producible by the process of the invention.

In a preferred embodiment of the present invention, the fibre degrades in a period of >6 months, for example more than 3 years, more preferably of from 6 to 18 months and particularly preferably of from 10 to 12 months.

Another preferred embodiment of the present invention envisages that the fibre is coilable.

In another preferred embodiment of the present invention, the proportion of functional groups from the organic acid that are covalently attached in the network is 30 to 80%, preferably 45 to 75% and more preferably 53 to 65%, based on the functional groups provided in step b).

Use

The present invention further relates to the use of the fibres of the invention or of fibre meshes made from these fibres.

Preference is given to use in the following fields:

Regenerative therapies, preferably as cell-support materials for the development of tissues or cell cultures or as light guides, more preferably in the field of minimally invasive surgery;

Microbiology, preferably the application or culture of bacteria, yeasts and fungi on the fibres;

Pharmaceutical uses, preferably for encapsulating or coupling active substances, enzymes or nanoparticles;

Cosmetics industry, preferably by integrating the fibres in cosmetic products;

Diagnostics, preferably in vitro and/or in vivo, more preferably for the covalent or adsorptive attachment of antibodies, aptamers and/or enzyme-substrate complexes;

Food industry, preferably to improve mouthfeel, more preferably by integrating flavourings, fats, proteins, enzymes, ions and food additives;

Filters, preferably for neutralizing waste water or for releasing ions into liquids;

Fibre reinforcement of materials, preferably in composite materials;

Optics, preferably in light therapy or endoscopy.

The invention is elucidated in more detail with reference to the examples that follow, without intending to restrict it to the specific embodiments shown here.

WORKING EXAMPLES

1) Methanesulfonic Acid 5 mol of tetraethoxysilane (Sigma Aldrich) was mixed in ethanolic solution (400 ml). To this sol was added dropwise, over a 2 h period, 0.02 mol of methanesulfonic acid (Sigma Aldrich) in a 0.1 N aqueous solution and the resulting mixture was stirred for a further 18 h at 40° C. This resulted in the covalent incorporation of the methanesulfonic acid into the Si—O framework (see below for demonstration of this).

906.5 g of solvent was then stripped from the sol and the sol was matured at −20° C. to a honey-like viscosity (21 Pa*s measured at 4° C.). The viscous liquid was transferred to a pressure vessel thermally equilibrated at −15° C. and forced with a pressure of 20 bar through a die plate having seven dies (die diameter: 150 μm). After a fall distance of 2.5 m, the fibres were collected and stored at 20% atmospheric humidity. The spinning conditions specified in the article "Nanostructured surfaces of biodegradable silica fibres enhance direct amoeboid cell migration in a microtubule-dependent process" by Martin Emmert, Patrick Witzel, Miranda Rothenburger-Glaubitt and Doris Heinrich, published in The Royal Society of Chemistry 2017, volume 7, pages 5708 to 5714, are likewise very well suited to the spinning of the fibres of the invention.

Figure 1:
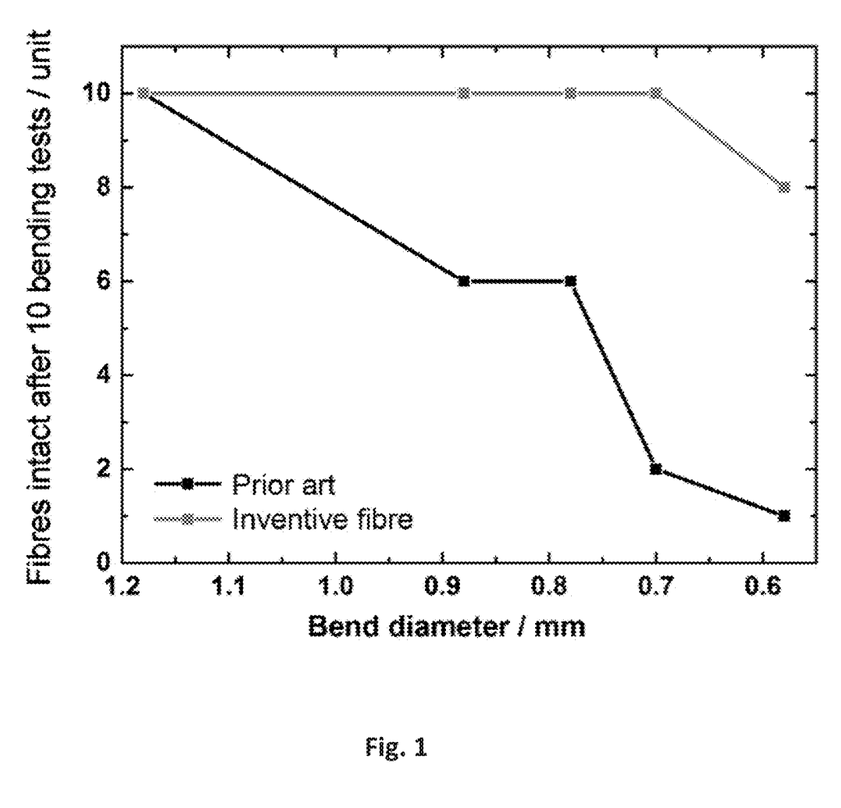
FIG. 1 depicts the results of bending tests on the fibers of the invention and of a prior art.

The fibres were stored at low atmospheric humidity and showed very flexible properties. For the test of flexible properties, a fibre of the invention was coiled around a cylindrical rod of varying diameters and examined to see whether the fibre breaks at the given diameter or remains intact. This test was carried out on a total of 10 different fibres and the number of intact fibres after the 10 tests was plotted for each rod diameter. The comparison system used was a fibre of the prior art produced according to DE 196 09 551 C1. As can be seen from FIG. 1, the fibre of the invention (MSA fibre) has greater flexibility than the fibre of the prior art ($HNO_3$ fibre) and breaks only at a diameter of <0.7 mm.

Figure 2:
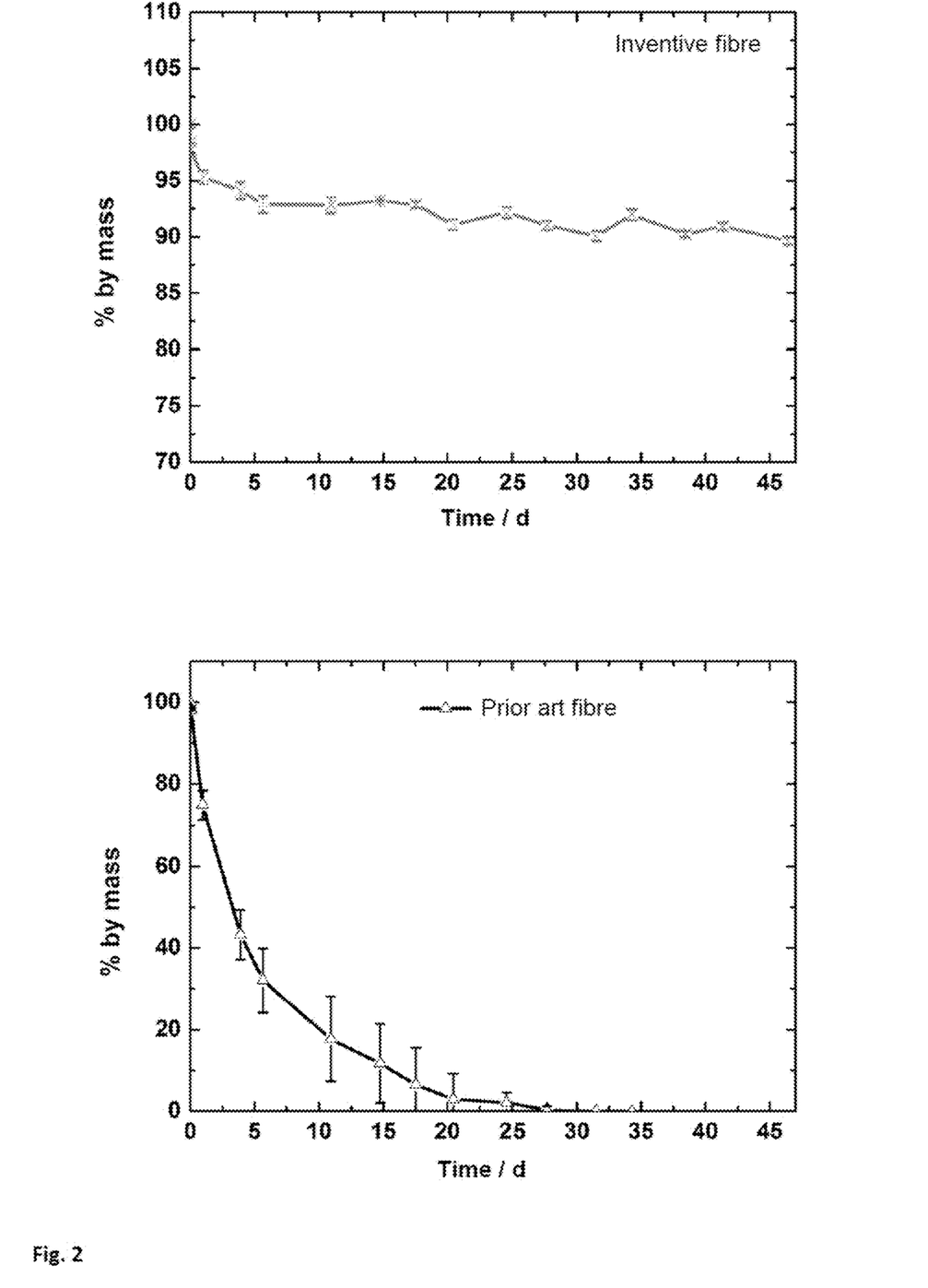
FIG. 2 depicts degradation profiles of the fibers of the invention and of a prior art.

FIG. 2 (top) shows the degradation profile of a fibre of the invention in phosphate-buffered saline (PBS) and the lower part of FIG. 2 shows the degradation profile of a fibre produced according to the prior art. The tests were carried out statically, i.e. the degradation medium was replaced on each measurement day. The degradation profile was generated gravimetrically by removing the fibres on the respective measurement day, drying to constant weight and determining the remaining fibre mass. The fibres were then returned to the degradation medium for further degradation.

It can be seen from the figures that the fibre of the invention degrades slowly, whereas the fibre of the prior art was completely degraded within just 5 weeks.

Figure 3:
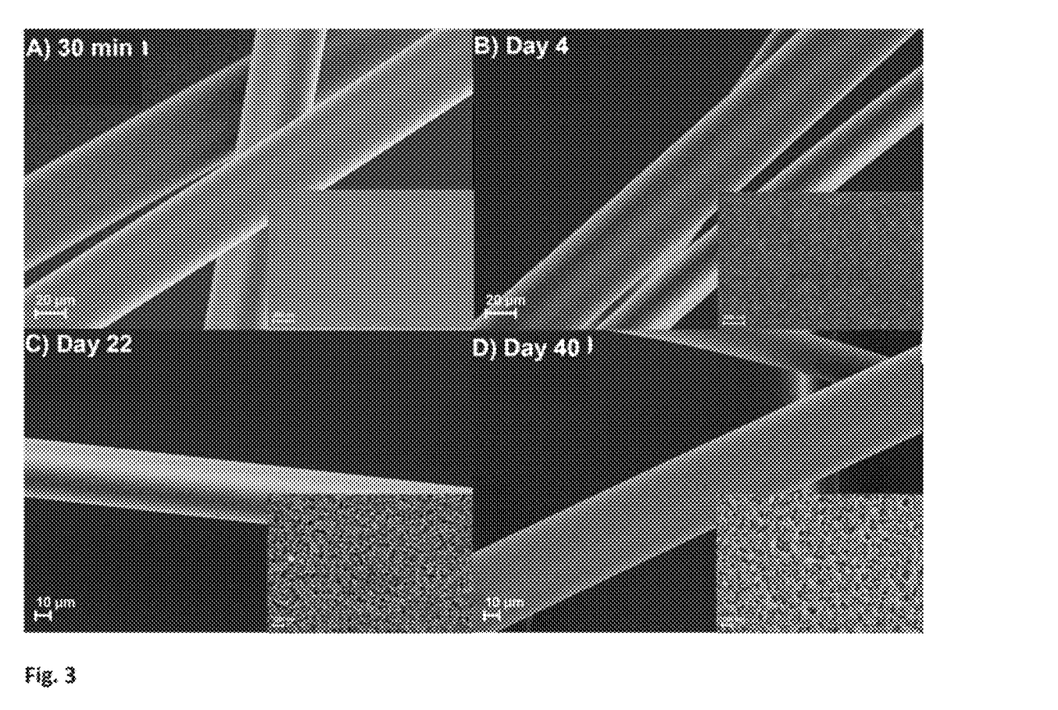
FIG. 3 depicts SEM images of the fibre of the invention after storage in PBS.

FIG. 3 shows SEM images of the fibre of the invention after storage in PBS for 30 minutes, 4 days, 22 days and 40 days. Progressive degradation is clearly visible.

Figure 4:
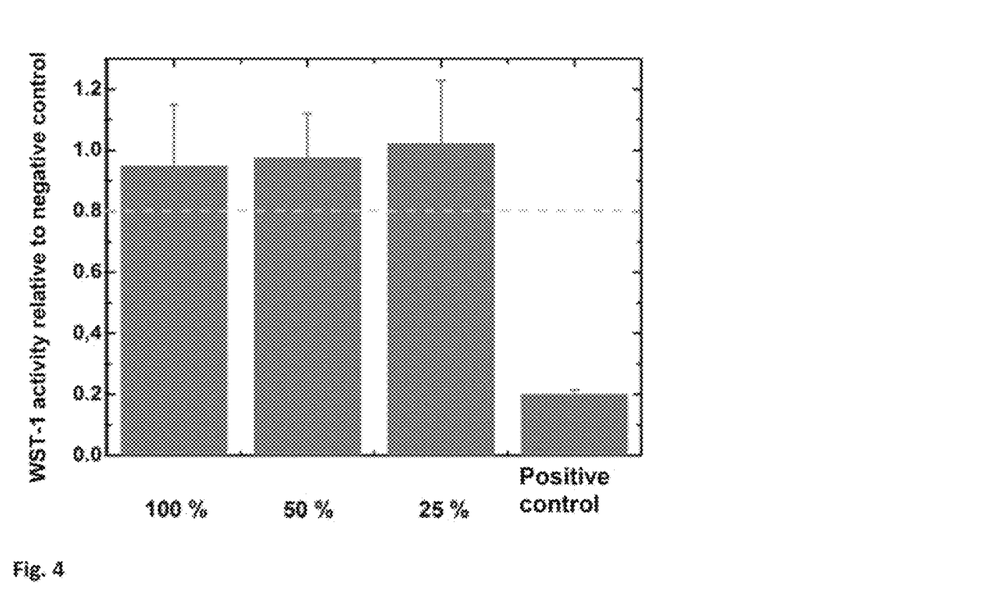
FIG. 4 depicts the biocompatibility of the fibre of the invention.

In addition, a biocompatibility test with the fibre of the invention was carried out in accordance with DIN ISO 10993-5. The data are summarized in FIG. 4 and the fibre of the invention is biocompatible, values over 80% being considered non-cytotoxic.

Figure 5:
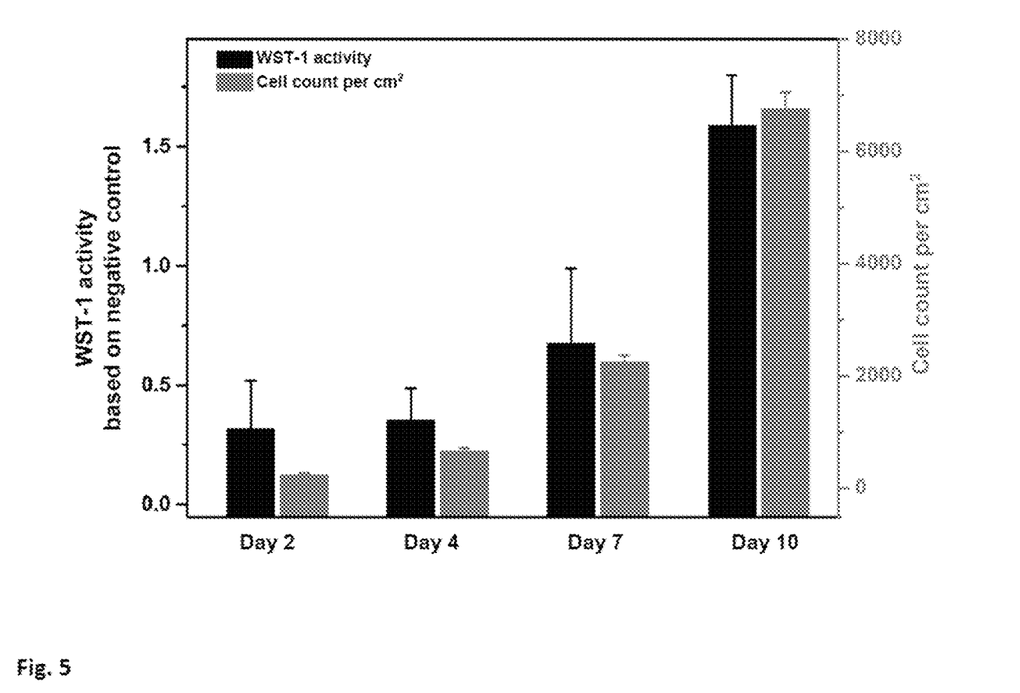
FIG. 5 depicts the results of cell-proliferation studies carried on the fibre of the invention.

FIG. 5 summarizes results of cell-proliferation studies with the fibre of the invention.

For this, 60 mg of fibre material was washed with phosphate-buffered saline (PBS) and populated with 50 000 human dermal fibroblasts (hdF) in a 12-well plate. The populated nonwovens were incubated in cell-culture medium (DMEM) containing 10% foetal calf serum for 2, 4, 7 and 10 days. On each measurement day, the fibres were transferred to a new multiwell plate and the WST-1 activity of the cells measured and the cell count determined. As a negative control, cells were incubated without fibres in a well containing DMEM (+10% FCS) and as a positive control with DMEM (+10% FCS) containing 1% sodium dodecyl sulfate (SDS).

It can be seen from the figure that human dermal fibroblasts proliferate much more rapidly on the fibre of the invention. Moreover, the fibre of the invention shows high cell metabolic activity.

As shown by thermogravimetric analyses in a synthetic air atmosphere coupled to a mass spectrometer (TGA-MS), $SO_x$ is liberated only at temperatures above 400° C. This demonstrates the covalent attachment of the sulfonic acid.

2) Para-Toluenesulfonic Acid 5 mol of tetraethoxysilane (Sigma Aldrich) was mixed in ethanolic solution (400 ml). To this sol was added dropwise, over a 2 h period, 0.02 mol of para-toluenesulfonic acid (Sigma Aldrich) in a 0.1 N aqueous solution and the resulting mixture was stirred for a further 18 h at 40° C. This resulted in the covalent incorporation of the para-toluenesulfonic acid into the Si—O framework.

906.5 g of solvent was then stripped from the sol and the sol was matured at −20° C. to a honey-like viscosity (22 Pa*s measured at 4° C.). The viscous liquid was transferred to a pressure vessel thermally equilibrated at −15° C. and forced with a pressure of 20 bar through a die plate having seven dies (die diameter: 150 μm). After a fall distance of 2.5 m, the fibres were collected and stored at 20% atmospheric humidity.

The invention claimed is:

1. A process for producing biodegradable fibres comprising the following steps:
   a) providing an alcoholic solution of a silane compound selected from the group consisting of tetraalkoxysilanes, trialkoxysilanes, halosilanes, and mixtures thereof;
   b) providing an aqueous solution of an organic acid selected from the group consisting of sulfonic acids, sulfuric esters, phosphonic acids, phosphoric esters, and mixtures thereof;
   c) combining the solutions provided in steps a) and b) and mixing for 4 hours to 1 week at a temperature of 20 to 70° C.;
   d) removing at least part of the alcohol from the mixture from step c) and cooling the concentrated mixture to a temperature of 20 to −25° C.;

e) storing the cooled mixture from step d) until a viscosity of 10 to 75 Pa·s is reached; and f) spinning the mixture from step e) into continuous fibres; wherein during steps c) to e), the silane compound undergoes crosslinking and at least part of the organic acid is incorporated into the resulting network via covalent bonds and/or contributes to the crosslinking.

2. The process according to claim 1, wherein the silane compound selected in step a) is a mixed or unmixed tetraalkoxysilane corresponding to the general formula $Si(OC_xH_{2x+1})_4$ where $x=1$-12, and/or the alcohol from step a) is a monohydric, dihydric or trihydric, branched or unbranched alcohol that can be aliphatic or aromatic.

3. The process according claim 1, wherein the organic acid in step b) is 0.01 to 1 N; and/or the content of organic acid in the aqueous solution from step b) is in the range from 0.01 to 2% by weight, based on the total weight of the solution.

4. The process according to claim 1, wherein the mixing in step c) is carried out by adding the aqueous solution of the organic acid dropwise to the alcoholic silane solution; or the mixing in step c) is carried out by adding the alcoholic silane solution dropwise to the aqueous solution of the organic acid; or the mixing in step c) is carried out by simultaneous combination of the alcoholic silane solution and the aqueous solution of the organic acid; and/or the mixing in step c) is carried out by stirring or agitation; and/or the mixture from step c) is stirred for 5 hours to 144 hours; and/or the temperature in step c) is 20 to 60° C.; and the pH of the mixture in step c) is <5.

5. The process according to claim 1, wherein during step d) 40 to 80% by weight of the solvent mixture, based on the total mass of mixture provided in step b), is removed; and/or the concentrated mixture from step d) is cooled to a temperature of 20 to −25° C.; and/or at least part of the water from step b) is also removed during step d).

6. The process according to claim 1, wherein step e) is carried out until a viscosity of 10 to 70 Pa·s is reached.

7. The process according to claim 1, wherein spinning is carried out with the application of pressure in the range from 10 to 60 bar.

8. The process according to claim 1, wherein the process comprises the following further process steps, which take place after step f):

g) cutting or die-cutting the continuous fibres obtained after spinning in step f), and/or h) sterilizing the fibres from step f) or g).

9. The process according to claim 1, wherein exactly one alcohol is used as solvent in step a) and/or exactly one silane compound is dissolved in the solution from step a); and/or an aqueous solution of exactly one organic acid is provided in step b).

10. The process according to claim 1, wherein the process is carried out as a continuous or batch-wise operation.

11. A biodegradable fibre produced by a process comprising the following steps:

a) providing an alcoholic solution of a silane compound selected from the group consisting of tetraalkoxysilanes, trialkoxysilanes, halosilanes, and mixtures thereof;

b) providing an aqueous solution of an organic acid selected from the group consisting of sulfonic acids, sulfuric esters, phosphonic acids, phosphoric esters, and mixtures thereof;

c) combining the solutions provided in steps a) and b) and mixing for 4 hours to 1 week at a temperature of 20 to 70° C.;

d) removing at least part of the alcohol from the mixture from step c) and cooling the concentrated mixture to a temperature of 20 to −25° C.;

e) storing the cooled mixture from step d) until a viscosity of 10 to 75 Pa·s is reached; and f) spinning the mixture from step e) into continuous fibres; wherein during steps c) to e), the silane compound undergoes crosslinking and at least part of the organic acid is incorporated into the resulting network via covalent bonds and/or contributes to the crosslinking.

12. The biodegradable fibre according to claim 11, wherein the fibre degrades in a period of >6 months.

13. The biodegradable fibre according to claim 11, wherein the fibre is coilable and/or the proportion of functional groups from the organic acid that are covalently attached in the network is 30 to 80%, based on the functional groups provided in step b).

14. A fibre mesh or filter comprising biodegradable fibres according to claim 11.

* * * * *